(12) United States Patent
Shennib et al.

(10) Patent No.: US 11,331,008 B2
(45) Date of Patent: *May 17, 2022

(54) HEARING TEST SYSTEM FOR NON-EXPERT USER WITH BUILT-IN CALIBRATION AND METHOD

(71) Applicant: K/S HIMPP, Lynge (DK)

(72) Inventors: Adnan Shennib, Oakland, CA (US); Victor Valenzuela, Hayward, CA (US)

(73) Assignee: K/S HIMPP, Lynge (DK)

( * ) Notice: Subject to any disclaimer, the term of this patent is extended or adjusted under 35 U.S.C. 154(b) by 218 days.

This patent is subject to a terminal disclaimer.

(21) Appl. No.: 16/544,721

(22) Filed: Aug. 19, 2019

(65) Prior Publication Data

US 2020/0100709 A1  Apr. 2, 2020

Related U.S. Application Data

(63) Continuation of application No. 14/846,003, filed on Sep. 4, 2015, now abandoned.
(Continued)

(51) Int. Cl.
*A61B 5/12* (2006.01)

(52) U.S. Cl.
CPC ...... *A61B 5/123* (2013.01); *A61B 2560/0223* (2013.01)

(58) Field of Classification Search
CPC .................. A61B 5/123; A61B 2560/0223; H04R 25/70; H04R 2225/023; H04R 25/656;
(Continued)

(56) References Cited

U.S. PATENT DOCUMENTS

| 4,759,070 A | 7/1988 | Voroba |
| 4,962,537 A | 10/1990 | Basel et al. |

(Continued)

FOREIGN PATENT DOCUMENTS

| EP | 2515303 A1 | 10/2012 |
| JP | 57188235 A | 11/1982 |

(Continued)

OTHER PUBLICATIONS

Internet Archive, World Health Organization website "Grades of Hearing Impairment". Retrieved from <https://web.archive.org/web/20121024120107/http://www.who.int/pbd/deafness/hearing_impairment_grades/en> on Aug. 27, 2015.
(Continued)

*Primary Examiner* — Patrick Fernandes
(74) *Attorney, Agent, or Firm* — Dorsey & Whitney LLP

(57) ABSTRACT

Disclosed herein are examples of methods and systems for performing a calibration check of a personal hearing test system using a built-in calibration cavity, particularly for use by a non-expert user outside the clinical environment. The hearing test system includes a one or more earpieces. The hearing test system further includes a portable test unit having an acoustic calibration cavity for accommodating the earpiece at least partially therein. The acoustic calibration cavity may include an opening along an exterior surface of the portable test unit. The acoustic calibration cavity receives an acoustic calibration stimuli and the microphone provided within the acoustic calibration cavity produces a calibration signal input for measuring and performing a calibration check, or an automatic self-calibration.

21 Claims, 9 Drawing Sheets

Related U.S. Application Data

(60) Provisional application No. 62/047,607, filed on Sep. 8, 2014.

(58) Field of Classification Search
CPC .... H04R 25/558; H04R 25/602; H04R 25/30; H04R 2430/01; H04R 2460/15; H04R 1/1066; H04R 2205/041; H04R 25/502; H04R 25/55; H04R 5/04; H04R 1/10; H04R 2201/10; H04R 2225/43; H04R 2420/07; H04R 25/353; H04R 25/407; H04R 25/43; H04R 25/48; H04R 5/033; H04M 1/2155; H04M 1/2475; H04M 1/6016; H04M 1/72591; G10L 15/01; G10L 21/02; H04S 2400/13
See application file for complete search history.

(56) References Cited

U.S. PATENT DOCUMENTS

| | | | |
|---|---|---|---|
| 5,197,332 A * | 3/1993 | Shennib | A61B 5/121 600/559 |
| 5,327,500 A | 7/1994 | Campbell | |
| 5,553,152 A | 9/1996 | Newton | |
| 5,645,074 A | 7/1997 | Shennib et al. | |
| 5,659,621 A | 8/1997 | Newton | |
| 5,701,348 A | 12/1997 | Shennib et al. | |
| 5,785,661 A | 7/1998 | Shennib et al. | |
| 5,928,160 A | 7/1999 | Clark | |
| 6,137,889 A | 10/2000 | Shennib et al. | |
| 6,212,283 B1 | 4/2001 | Fletcher et al. | |
| 6,319,207 B1 | 11/2001 | Naidoo | |
| 6,359,993 B2 | 3/2002 | Brimhall | |
| 6,367,578 B1 | 4/2002 | Shoemaker | |
| 6,379,314 B1 | 4/2002 | Horn | |
| 6,382,346 B2 | 5/2002 | Brimhall et al. | |
| 6,428,485 B1 | 8/2002 | Rhe | |
| 6,447,461 B1 * | 9/2002 | Eldon | A61B 5/121 600/559 |
| 6,473,513 B1 | 10/2002 | Shennib et al. | |
| 6,522,988 B1 | 2/2003 | Hou | |
| 6,546,108 B1 | 4/2003 | Shennib et al. | |
| 6,674,862 B1 | 1/2004 | Magilen | |
| 6,724,902 B1 | 4/2004 | Shennib et al. | |
| 6,816,601 B2 | 11/2004 | Lin et al. | |
| 6,840,908 B2 | 1/2005 | Edwards et al. | |
| 6,937,735 B2 | 8/2005 | DeRoo et al. | |
| 6,940,988 B1 | 9/2005 | Shennib et al. | |
| 6,978,155 B2 | 12/2005 | Berg | |
| 7,010,137 B1 | 3/2006 | Leedom et al. | |
| 7,016,511 B1 | 3/2006 | Shennib | |
| 7,037,274 B2 | 5/2006 | Thoraton et al. | |
| 7,113,611 B2 | 9/2006 | Leedom et al. | |
| 7,215,789 B2 | 5/2007 | Shennib et al. | |
| 7,260,232 B2 | 8/2007 | Shennib | |
| 7,298,857 B2 | 11/2007 | Shennib et al. | |
| 7,310,426 B2 | 12/2007 | Shennib et al. | |
| 7,321,663 B2 | 1/2008 | Olsen | |
| 7,362,875 B2 | 4/2008 | Saxton et al. | |
| 7,403,629 B1 | 7/2008 | Aceti et al. | |
| 7,424,123 B2 | 9/2008 | Shennib et al. | |
| 7,424,124 B2 | 9/2008 | Shennib et al. | |
| 7,580,537 B2 | 8/2009 | Urso et al. | |
| 7,664,282 B2 | 2/2010 | Urso et al. | |
| 7,854,704 B2 | 12/2010 | Givens et al. | |
| 7,913,696 B2 | 3/2011 | Purcell et al. | |
| 7,945,065 B2 | 5/2011 | Menzl et al. | |
| 8,073,170 B2 | 12/2011 | Kondo et al. | |
| 8,077,890 B2 | 12/2011 | Schumaier | |
| 8,155,361 B2 | 4/2012 | Schindler | |
| 8,184,842 B2 | 5/2012 | Howard et al. | |
| 8,243,972 B2 | 8/2012 | Latzel | |
| 8,284,968 B2 | 10/2012 | Schumaier | |
| 8,287,462 B2 | 10/2012 | Givens et al. | |
| 8,340,335 B1 | 12/2012 | Shennib | |
| 8,379,871 B2 | 2/2013 | Michael et al. | |
| 8,396,237 B2 | 3/2013 | Schumaier | |
| 8,447,042 B2 | 5/2013 | Gurin | |
| 8,467,556 B2 | 6/2013 | Shennib et al. | |
| 8,503,703 B2 | 8/2013 | Eaton | |
| 8,571,247 B1 | 10/2013 | Oezer | |
| 8,718,306 B2 | 5/2014 | Gommel et al. | |
| 8,798,301 B2 | 8/2014 | Shennib | |
| 8,855,345 B2 | 10/2014 | Shennib et al. | |
| 9,031,247 B2 | 5/2015 | Shennib | |
| 9,060,233 B2 | 6/2015 | Shennib et al. | |
| 9,078,075 B2 | 7/2015 | Shennib et al. | |
| 9,107,016 B2 | 8/2015 | Shennib | |
| 9,253,583 B2 | 2/2016 | Blamey et al. | |
| 9,326,706 B2 | 5/2016 | Shennib | |
| 9,439,008 B2 | 9/2016 | Shennib | |
| 9,532,152 B2 | 12/2016 | Shennib et al. | |
| 9,788,126 B2 | 10/2017 | Shennib et al. | |
| 9,894,450 B2 | 2/2018 | Shennib | |
| 9,918,171 B2 | 3/2018 | Shennib | |
| 10,045,128 B2 | 8/2018 | Shennib | |
| 10,085,678 B2 | 10/2018 | Shennib | |
| 2001/0008560 A1 | 7/2001 | Stonikas et al. | |
| 2001/0009019 A1 | 7/2001 | Armitage | |
| 2001/0040973 A1 | 11/2001 | Fritz et al. | |
| 2001/0051775 A1 | 12/2001 | Rho | |
| 2002/0015506 A1 * | 2/2002 | Aceti | H04R 25/70 381/314 |
| 2002/0027996 A1 | 3/2002 | Leedom et al. | |
| 2002/0085728 A1 | 7/2002 | Shennib et al. | |
| 2003/0007647 A1 | 1/2003 | Nielsen et al. | |
| 2003/0078515 A1 | 4/2003 | Menzel et al. | |
| 2004/0028250 A1 | 2/2004 | Shim | |
| 2004/0073136 A1 | 4/2004 | Thornton et al. | |
| 2004/0122873 A1 | 6/2004 | Wright, Jr. et al. | |
| 2004/0136555 A1 | 7/2004 | Enzmann | |
| 2004/0165742 A1 | 8/2004 | Shennib et al. | |
| 2005/0094822 A1 | 5/2005 | Swartz | |
| 2005/0190938 A1 | 9/2005 | Shennib et al. | |
| 2005/0226447 A1 | 10/2005 | Miller, III | |
| 2005/0245991 A1 | 11/2005 | Faltys et al. | |
| 2005/0249370 A1 | 11/2005 | Shennib et al. | |
| 2005/0259829 A1 | 11/2005 | Van den Heuvel et al. | |
| 2005/0259840 A1 | 11/2005 | Gable et al. | |
| 2005/0283263 A1 | 12/2005 | Eaton et al. | |
| 2006/0094981 A1 | 5/2006 | Camp | |
| 2006/0210090 A1 | 9/2006 | Shennib | |
| 2006/0210104 A1 | 9/2006 | Shennib et al. | |
| 2006/0291683 A1 | 12/2006 | Urso et al. | |
| 2007/0009126 A1 | 1/2007 | Fischer et al. | |
| 2007/0019834 A1 | 1/2007 | Nielson | |
| 2007/0071252 A1 | 3/2007 | Burger et al. | |
| 2007/0071265 A1 | 3/2007 | Leedom et al. | |
| 2007/0076909 A1 | 4/2007 | Roeck et al. | |
| 2007/0189545 A1 | 8/2007 | Geiger et al. | |
| 2007/0204695 A1 * | 9/2007 | Gross | A61B 5/121 73/585 |
| 2007/0223721 A1 * | 9/2007 | Stern | H04R 5/04 381/74 |
| 2007/0237346 A1 | 10/2007 | Fichti et al. | |
| 2008/0137891 A1 | 6/2008 | Vohringer | |
| 2008/0240452 A1 | 10/2008 | Burrows et al. | |
| 2008/0273726 A1 | 11/2008 | Yoo et al. | |
| 2008/0298600 A1 | 12/2008 | Poe et al. | |
| 2009/0103764 A1 * | 4/2009 | Stiehl | H04R 1/1016 381/380 |
| 2009/0220099 A1 | 9/2009 | Voix et al. | |
| 2010/0040250 A1 | 2/2010 | Gerbert | |
| 2010/0119094 A1 | 5/2010 | Sjursen et al. | |
| 2010/0145411 A1 | 6/2010 | Spitzer | |
| 2010/0191143 A1 | 7/2010 | Ganter | |
| 2010/0226520 A1 | 9/2010 | Feeley et al. | |
| 2010/0239112 A1 | 9/2010 | Howard et al. | |
| 2010/0268115 A1 | 10/2010 | Wasden et al. | |
| 2010/0284556 A1 | 11/2010 | Young | |
| 2010/0290654 A1 | 11/2010 | Wiggins et al. | |
| 2011/0009770 A1 * | 1/2011 | Margolis | A61B 5/121 600/559 |
| 2011/0058697 A1 | 3/2011 | Shennib et al. | |

(56) References Cited

U.S. PATENT DOCUMENTS

| | | | |
|---|---|---|---|
| 2011/0100127 A1* | 5/2011 | Beck | A61B 5/121 |
| | | | 73/585 |
| 2011/0176686 A1 | 7/2011 | Zaccaria | |
| 2011/0188689 A1 | 8/2011 | Beck et al. | |
| 2011/0190658 A1 | 8/2011 | Sohn et al. | |
| 2011/0200216 A1 | 8/2011 | Lee et al. | |
| 2011/0206225 A1 | 8/2011 | Møller et al. | |
| 2011/0237103 A1* | 9/2011 | Harlan | H01R 13/2414 |
| | | | 439/271 |
| 2011/0319018 A1 | 12/2011 | Kroman | |
| 2012/0051569 A1* | 3/2012 | Blamey | H04R 25/305 |
| | | | 381/314 |
| 2012/0095528 A1 | 4/2012 | Miller, III et al. | |
| 2012/0130271 A1 | 5/2012 | Margolis et al. | |
| 2012/0157876 A1 | 6/2012 | Bang et al. | |
| 2012/0177212 A1 | 7/2012 | Hou et al. | |
| 2012/0177235 A1 | 7/2012 | Solum | |
| 2012/0183164 A1 | 7/2012 | Foo et al. | |
| 2012/0183165 A1 | 7/2012 | Foo et al. | |
| 2012/0189140 A1 | 7/2012 | Hughes | |
| 2012/0213393 A1 | 8/2012 | Foo et al. | |
| 2012/0215532 A1 | 8/2012 | Foo et al. | |
| 2012/0263330 A1 | 10/2012 | Larsen | |
| 2012/0285470 A9 | 11/2012 | Sather et al. | |
| 2012/0288107 A1 | 11/2012 | Lamm et al. | |
| 2012/0302859 A1 | 11/2012 | Keefe | |
| 2013/0010406 A1 | 1/2013 | Stanley | |
| 2013/0177188 A1 | 7/2013 | Apfel et al. | |
| 2013/0182877 A1 | 7/2013 | Angst et al. | |
| 2013/0223666 A1 | 8/2013 | Michel et al. | |
| 2013/0243209 A1 | 9/2013 | Zurbruegg et al. | |
| 2013/0243227 A1 | 9/2013 | Kinsbergen et al. | |
| 2013/0243229 A1 | 9/2013 | Shennib et al. | |
| 2013/0294631 A1 | 11/2013 | Shennib et al. | |
| 2014/0003639 A1 | 1/2014 | Shennib et al. | |
| 2014/0150234 A1 | 6/2014 | Shennib et al. | |
| 2014/0153761 A1 | 6/2014 | Shennib et al. | |
| 2014/0153762 A1 | 6/2014 | Shennib et al. | |
| 2014/0193008 A1 | 7/2014 | Zukic | |
| 2014/0254843 A1 | 9/2014 | Shennib | |
| 2014/0254844 A1 | 9/2014 | Shennib | |
| 2015/0023512 A1 | 1/2015 | Shennib | |
| 2015/0023534 A1 | 1/2015 | Shennib | |
| 2015/0023535 A1 | 1/2015 | Shennib | |
| 2015/0025413 A1 | 1/2015 | Shennib | |
| 2015/0215714 A1 | 7/2015 | Shennib et al. | |
| 2015/0256942 A1 | 9/2015 | Kinsbergen et al. | |
| 2016/0066822 A1 | 3/2016 | Shennib et al. | |
| 2016/0080872 A1 | 3/2016 | Shennib et al. | |
| 2016/0166181 A1 | 6/2016 | Shennib | |
| 2016/0198271 A1 | 7/2016 | Shennib | |
| 2016/0337770 A1 | 11/2016 | Shennib | |
| 2016/0350821 A1 | 12/2016 | Shennib et al. | |
| 2017/0070833 A1 | 3/2017 | Shennib | |
| 2017/0164124 A1 | 6/2017 | Shennib | |

FOREIGN PATENT DOCUMENTS

| | | |
|---|---|---|
| JP | 06105828 A | 4/1994 |
| JP | H10126895 A | 5/1998 |
| JP | 2002191581 A | 7/2002 |
| JP | 2002259714 A | 9/2002 |
| JP | 2005168856 A | 6/2005 |
| JP | 2005286876 A | 10/2005 |
| JP | 2007028609 A | 2/2007 |
| JP | 2008109594 A | 5/2008 |
| KR | 1020050114861 A | 12/2005 |
| KR | 100955033 B1 | 4/2010 |
| KR | 1020100042370 A | 4/2010 |
| WO | 99/07182 A2 | 2/1999 |
| WO | 2006136174 A2 | 12/2006 |
| WO | 2010/091480 A1 | 8/2010 |
| WO | 2011128462 A2 | 10/2011 |
| WO | 2015009559 A1 | 1/2015 |
| WO | 2015009561 A1 | 1/2015 |
| WO | 2015009564 A1 | 1/2015 |
| WO | 2015009569 A1 | 1/2015 |
| WO | 2016044178 A1 | 3/2016 |
| WO | 2017096279 A1 | 6/2017 |

OTHER PUBLICATIONS

"Basic Guide to In Ear Canalphones", Internet Archive, Head-Fi. org, Jul. 1, 2012. Retrieved from http://web.archive.org/web/20120701013243/http:www.head-fi.org/a/basic-guide-to-in-ear-canalphones> on Apr. 14, 2015.

"DB HL—Sensitivity to Sound—Clinical Audiograms", Internet Archive, AuditoryNeuroscience.com, Apr. 20, 2013. Retrieved from <https://web.archive.org/web/20130420060438/http://www.auditoryneuroschience.com/acoustics/clinical_audiograms>on Apr. 14, 2015.

"Lyric User Guide", http://www.phonak.com/content/dam/phonak/b2b/C_M_tools/Hearing_Instruments/Lyric/documents/02-gb/Userguide_Lyric_V8_GB_FINAL_WEB.pdf, Jul. 2010.

"Methods for Calculation of the Speech Intelligibility Index", American National Standards Institute, Jun. 6, 1997.

"Specification for Audiometers", American National Standards Institute, Nov. 2, 2010.

"The Audiogram", Internet Archive, ASHA.org, Jun. 21, 2012. Retrieved from <https:/web.archive.org/web/20120621202942/http://www.asha.org/public/hearing/Audiogram> on Apr. 14, 2015.

"User Manual—2011", AMP Personal Audio Amplifiers.

Abrams, "A Patient-adjusted Fine-tuning Approach for Optimizing the Hearing Aid Response", The Hearing Review, Mar. 24, 2011, 1-8.

Amlani, et al., "Methods and Applications of the Audibility Index in Hearing Aid Selection and Fitting", Trends in Amplication 6.3 (2002) 81. Retrieved from <https://www.ncbi.nlm.nih.gov/pmc/articles/PMC4168961/> on Apr. 14, 2015.

ASHA, "Type, Degree, and Configuration of Hearing Loss", American Speech-Language-Hearing Association; Audiology Information Series, May 2011, 1-2.

Convery, et al., "A Self-Fitting Hearing Aid: Need and Concept", http://tia.sagepubl.com, Dec. 4, 2011, 1-10.

Franks, "Hearing Measurements", National Institute for Occupational Safety and Health, Jun. 2006, 183-232.

Kiessling, "Hearing aid fitting procedures—state-of-the-art and current issues", Scandinavian Audiology vol. 30, Suppl 52, 2001, 57-59.

Kryter, "Methods for the calculation and use of the articulation index", The Journal of the Acoustical Society of America 34.11 (1962): 1689-1697. Retrieved from <http://dx.doi.org/10.1121/1.1909094> on Aug. 27, 2015.

NHANES, "Audiometry Procedures Manual", National Health and Nutrition Examination Survey, Jan. 2003, 1-105.

Sindhusake, et al., "Validation of self-reported hearing loss. The Blue Mountains hearing study", International Journal of Epidemiology 30.6 (2001): 1371-1378. Retrieved from <http://ije.oxfordjournals.org/content/30/6/1371.full> on Aug. 27, 2015.

Traynor, "Prescriptive Procedures", www.rehab.research.va.gov/mono/ear/traynor.htm, Jan. 1999, 1-16.

World Health Organization, "Deafness and Hearing Loss", www.who.int/mediacentre/factsheets/fs300/en/index.htmi, Feb. 2013, 1-5.

\* cited by examiner

HEARING TEST SYSTEM FOR NON-EXPERT USER WITH BUILT-IN CALIBRATION AND METHOD

CROSS-REFERENCE TO RELATED APPLICATIONS

This application is a continuation of U.S. application Ser. No. 14/846,003 filed Sep. 4, 2015 which claims the benefit under 35 U.S.C. 119 of the earlier filing date of U.S. Provisional Application No. 62/047,607 entitled "HEARING TEST SYSTEM FOR NON-EXPERT USER WITH BUILT-IN CALIBRATION AND METHOD," filed Sep. 8, 2014. The aforementioned applications are hereby incorporated by reference in their entirety, for any purpose.

This application is related to U.S. Pat. No. 8,467,556, titled, "CANAL HEARING DEVICE WITH DISPOSABLE BATTERY MODULE"; U.S. Pat. No. 9,326,706, titled, "HEARING PROFILE TEST SYSTEM AND METHOD"; U.S. Pat. No. 9,031,247, titled, "HEARING AID FITTING SYSTEMS AND METHODS USING SOUND SEGMENTS REPRESENTING RELEVANT SOUNDSCAPE"; U.S. Pat. No. 9,107,016, titled. "INTERACTIVE HEARING AID FITTING SYSTEM AND METHODS"; U.S. Pat. No. 9,439,008, titled, "ONLINE HEARING AID FITTING SYSTEM AND METHODS FOR NON-EXPERT USER"; U.S. Pat. No. 10,085,678, titled, "METHOD FOR RAPIDLY DETERMINING WHO GRADING OF HEARING IMPAIRMENT"; U.S. Pat. No. 10,045,128, titled, "HEARING DEVICE TEST SYSTEM FOR NON-EXPERT USER AT HOME AND NON-CLINICAL SETTINGS"; all of which are incorporated herein by reference in their entirety for any purpose.

TECHNICAL FIELD

Examples described herein relate to hearing testing, and more particularly methods and systems for performing a calibration check of a hearing test system using a built-in calibration system of the hearing test system.

BACKGROUND

Pure tone audiometry may be considered as the gold standard for hearing assessment. It relies on identifying the threshold of hearing for an individual, generally, using tonal sounds generated by instrumentation designed for clinical use by a hearing professional. The instrumentation and accessories for standard hearing tests in accordance with audiometry standards, such as ANSI S3.6, are generally specialized electro-medical devices for use in clinical settings. For example, to obtain a valid threshold of hearing and generate an audiogram report, tests are generally performed in specialized sound-isolated rooms, often referred to as a "sound room," to reduce noise levels present in the environment generally to that below the threshold of normal hearing. The combined cost of a sound room and clinical instrumentation for standard audiogram testing can easily exceed $20,000. These systems, with methods and processes associated thereto, are generally not suitable for self-administration by a hearing test consumer in home settings.

To circumvent some of the limitations of conventional hearing evaluation methods, automated, computer-based hearing evaluation methods have been proposed, including self-administered online tests using personal computers. These tests are often inadequate due to their inaccuracy, often caused by audio characteristics of consumer electronics not meeting the standards of audiometric testing. For example, consumer electronics, such as a sound card, may introduce unacceptable total harmonic distortion (THD), unpredictable frequency response, excessive signal noise, and/or excessive cross-over distortion. The sources of adverse audio characteristics can be attributed to the sound card, the speaker, consumer headphones, cabling, connectors, etc. In addition to the aforementioned obstacles related to audio characteristics, the calibration of acoustic signals emanating from a transducer (a consumer earphone, for example) represents a daunting challenge, preventing accurate hearing evaluation by a lay consumer using a personal computer, or a personal electronic device. Further, the transducer may not be easily recalibrated.

In order to use the internal speakers of a computing device or headphones, individual calibration for each transducer is generally required. The calibration data used to compensate for transducer variability may be stored in memory. The calibration data may also take into consideration the variability of the electronics of the hearing test system.

Over time, components of the hearing test system may be damaged or may drift, resulting in inaccurate sound level presentation during a hearing test. One method of checking the sound level produced by the hearing tester is to check the voltage levels of signals being delivered to the test transducer. However, this calibration check may not take into account the degradation or damage to the acoustics of the transducer element. Periodic calibration is generally required to ensure the hearing test acoustic output remains within the calibration range.

SUMMARY

The present disclosure relates to hearing test systems with built in self-calibration and calibration check capabilities and methods for calibration of hearing test systems. A hearing test system according to the present disclosure may include a headphone including one or more earpieces. One or more of the earpieces may produce an acoustic hearing test stimuli, e.g., for use during administration of a hearing test, and/or an acoustic calibration stimuli, e.g. for use during calibration or calibration check of the hearing test system. The acoustic calibration stimuli may be produced using production calibration data.

The hearing test system may include a portable test unit including an acoustic calibration cavity, a microphone, and audio processing electronics. The acoustic calibration cavity may include a first opening along an exterior surface of the portable test unit for receiving the earpiece, and a second opening. The microphone may be acoustically coupled to the acoustic calibration cavity at the second opening. The microphone may receive acoustic calibration stimuli from the earpiece and produce a calibration signal input in response to the acoustic calibration stimuli. The audio processing electronics may receive the calibration signal input from the microphone. The audio processing electronics may produce and deliver a calibration signal to the earpiece for producing the acoustic calibration stimuli when the earpiece is placed at least partially within the acoustic calibration cavity.

The hearing test system may include a processor communicatively coupled to the audio processing electronics and configured to determine a calibration level responsive to receipt of the calibration signal input. The processor may validate the calibration of the hearing test system by comparing the measured calibration level with a reference level. The reference level may be stored in memory of any of a remote server, a client computer, and the portable test unit.

In some examples, the processor may adjust production calibration data based on the measured calibration level.

In some examples, the hearing test system may include a computing device coupled to the portable test unit. The computing device may execute a hearing test software application stored locally or remotely. The computing device may perform a calibration check or self-calibration of the hearing test system when the earpiece is provided at least partially within the acoustic calibration cavity.

BRIEF DESCRIPTION OF THE DRAWINGS

The above and still further objectives, features, aspects and attendant advantages of the present invention will become apparent from the following detailed description of certain preferred and alternate embodiments and method of manufacture and use thereof, including the best mode presently contemplated of practicing the invention, when taken in conjunction with the accompanying drawings, in which.

DETAILED DESCRIPTION

Figure 1:
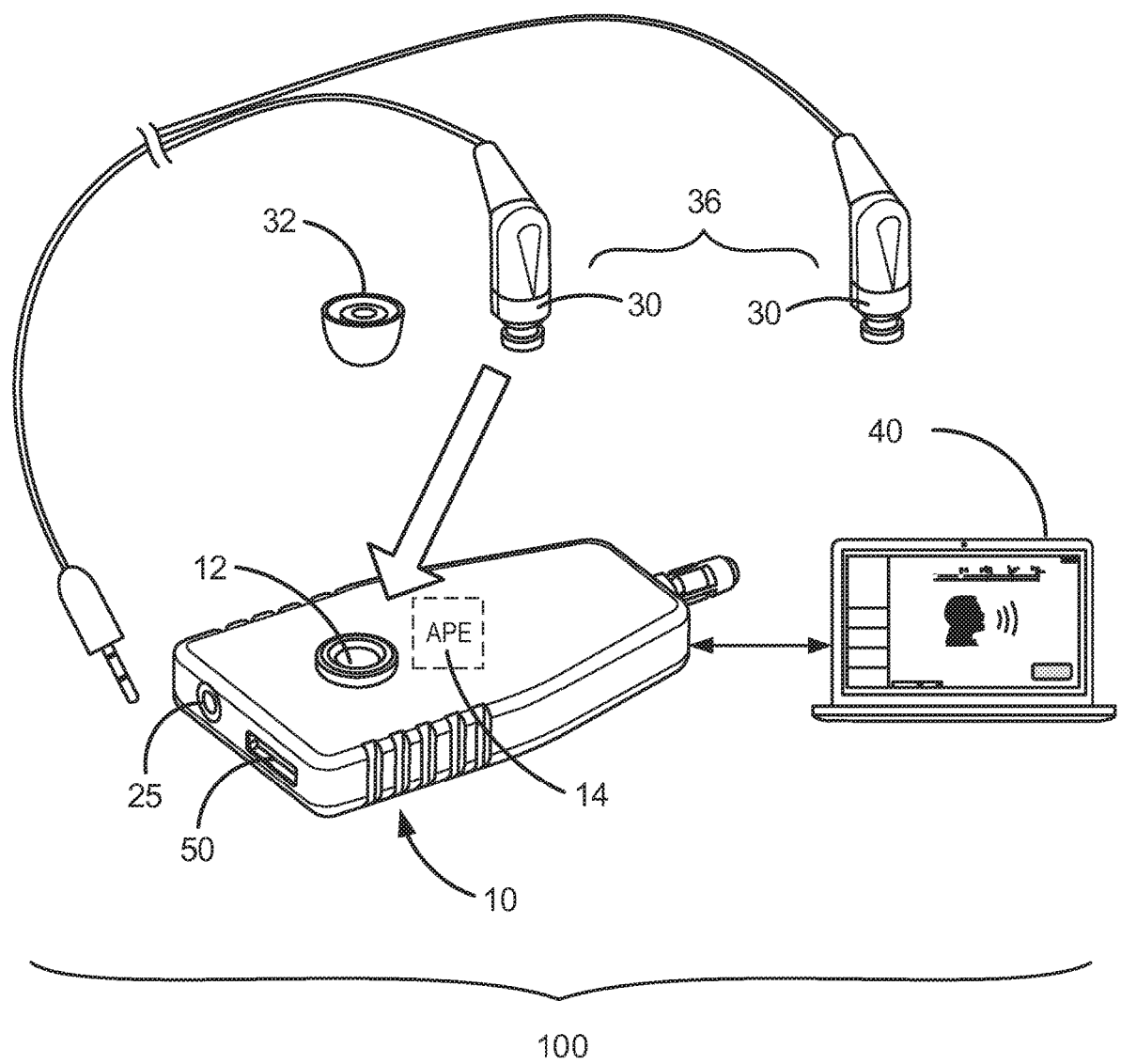
FIG. 1 is a schematic view of a hearing test system including a portable test unit communicatively coupled to a computing device (e.g., a personal computer), according to some examples.

Certain details are set forth below to provide a sufficient understanding of embodiments of the invention. Some embodiments, however, may not include all details described. In some instances, well-known structures may not be shown in order to avoid unnecessarily obscuring the described embodiments of the invention.

The present disclosure describes hearing test systems and methods for calibrating or checking a calibration of a hearing test system or components thereof. A hearing test system according to the present disclosure includes a portable test unit with a built-in calibration cavity. The hearing test system may be particularly suitable for personal use, for example for use by a non-expert user outside the clinical environment. A hearing test system according to examples disclosed herein may mitigate the need for a calibration check or calibration by a hearing professional, a calibration service technician, or other third party. Hearing test systems as described herein may empower consumers to self-administer a hearing test and/or a calibration check of a hearing test system at home, or generally at non-clinical settings such as an office, a nursing home, a community center, a drug store, a pharmacy, etc. In some examples, a calibration of a hearing test system may be checked automatically without resorting to sending some or all components of the hearing test system (e.g., a portable test unit) to the manufacturer or a service center. In some examples, calibration data associated with a hearing test system may be automatically adjusted to recalibrate the hearing test system after a calibration check.

FIGS. 1-6 and 9 are views of a hearing test system according to some examples of the present disclosure. With reference now to FIGS. 1-6 and 9, the hearing test system 100 includes a portable test unit 10 and an earpiece 30. The earpiece 30 may be one of a pair of earpieces of a headphone 36. Headphone 36 typically includes two earpieces 30 for testing right and left ears of an individual. Each earpiece 30 may couple with an ear tip 32 for secure fit in an ear of a user 1 and for attenuating noise in the non-test ear. The ear tips 32 may be provided in an assortment of sizes for fitting in various ear canal sizes. The ear tips 32 may be made from a compliant material, such as silicone or neoprene, for providing a comfortable fit in an ear of a user 1. In some examples, the portable test unit 10 may be handheld or wearable. The portable test unit 10 may include a wired or wireless programming interface 50 for programming a programmable hearing device 60. The portable test unit 10 includes an acoustic calibration cavity 12 for accommodating the earpiece 30 at least partially therein. The acoustic calibration cavity 12 of portable test unit 10 may be used to perform a calibration check or a self-calibration of the hearing test system 100, as will be described in further detail below.

Figure 9:
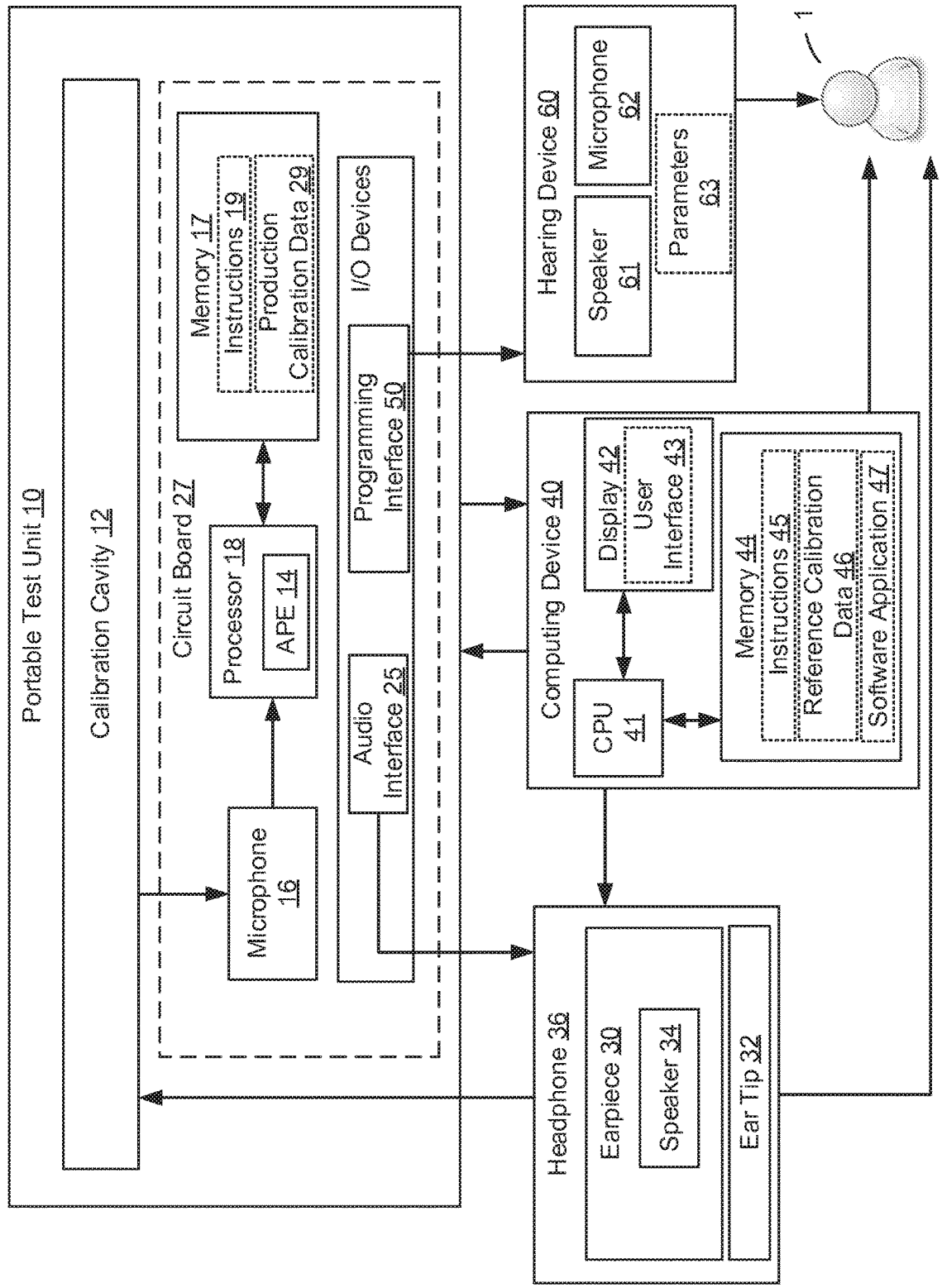
FIG. 9 is a schematic view of a hearing test system including a portable test unit comprising a calibration cavity along an exterior surface of the portable test unit, according to some examples.

The hearing test system 100, for example as shown in FIG. 9, may be used to administer a hearing test. During a hearing test, the earpiece 30 may receive an audio signal representative of an acoustic test stimuli or audible instructions for a hearing test. Earpiece 30 may produce the acoustic test stimuli or audible instructions for the hearing test, for example by audio streaming from a computing device 40. For example, during a hearing test, the headphone 36 may be communicatively coupled to a computing device 40 and may receive the audio signal from the computing device 40. The earpiece 30 may produce an acoustic test stimuli in response to the audio signal received from the computing device 40. In some examples, the headphone 36 may be communicatively coupled to the portable test unit 10 via an audio interface, for example an audio jack 25, as described herein. The portable test unit 10 may send the test audio signal to the headphone 36 and the earpiece 30 may produce an acoustic test stimuli in response to the test audio signal received from the portable test unit 10. A level of the audio signal generated may be set by the portable test unit 10 based on calibration data stored in memory (e.g., memory 17 of the portable test unit 10) or based on calibration data stored elsewhere (e.g., memory of a computing device communicatively coupled to portable test unit 10, or memory of a remote server). The acoustic test stimuli may be generated using a speaker 34 of the earpiece 30.

A hearing test system according to the present disclosure (e.g. hearing test system 100) may be configured to provide hearing evaluation at a suprathreshold range of hearing with respect to normal hearing ability. In some examples, hearing test system 100 may be operable to administer a hearing evaluation which includes acoustic test stimuli at loudness levels above 20 dB HL and step levels of at least 10 dB. In some examples, the headphone 36 may transmit a sequence of calibrated acoustic test stimuli at suprathreshold loudness levels at frequency bands within an audiometric frequency range. Audibility of a user at each test frequency band may be registered by the hearing test system. In some examples, the hearing test system may present a computed hearing profile score to the user 1 based on the user's minimum audibility level at each test frequency.

Figure 7:
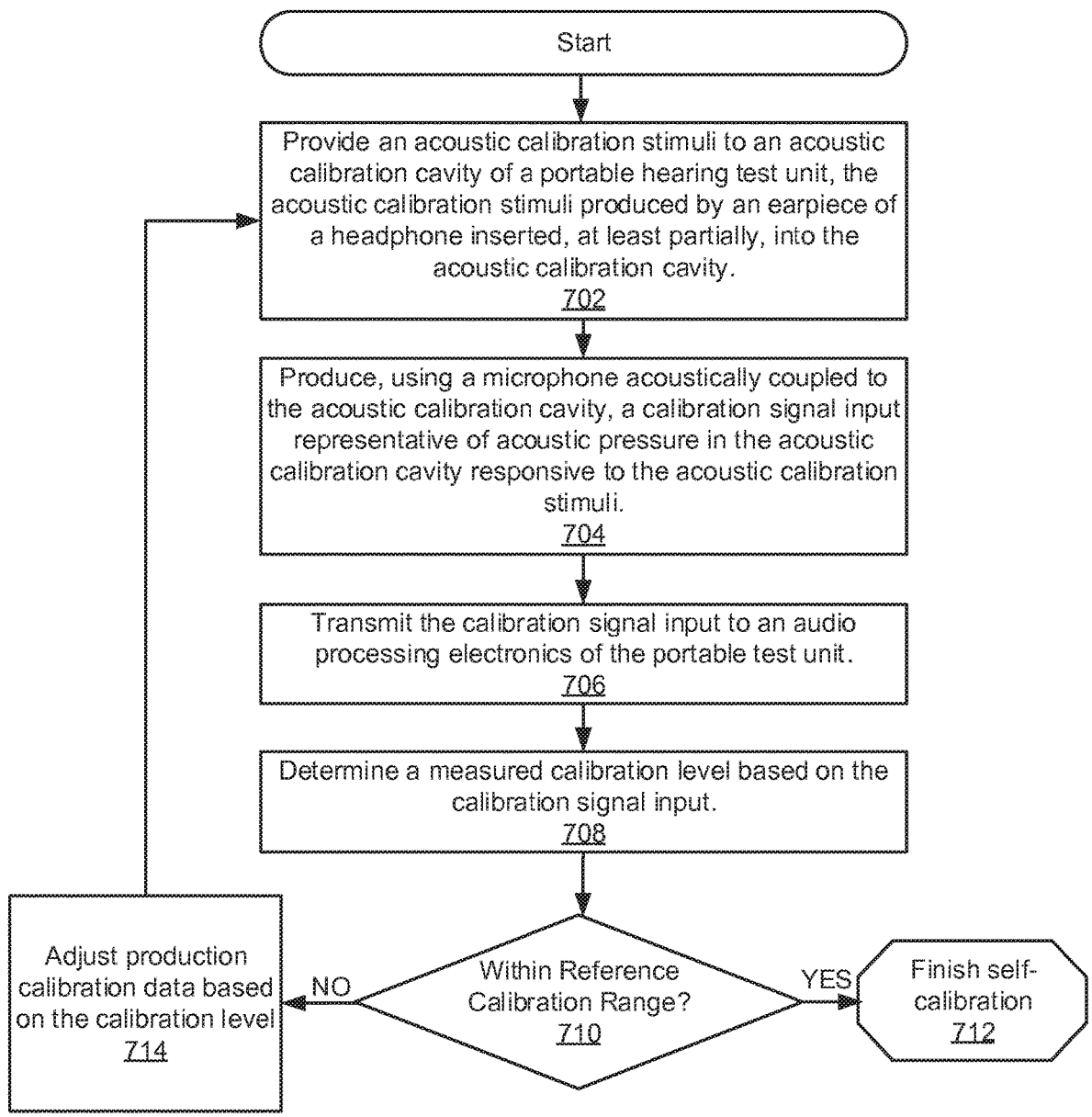
FIG. 7 is a flow chart representation for a self-calibration of a hearing test system, according to some examples.
Figure 8:
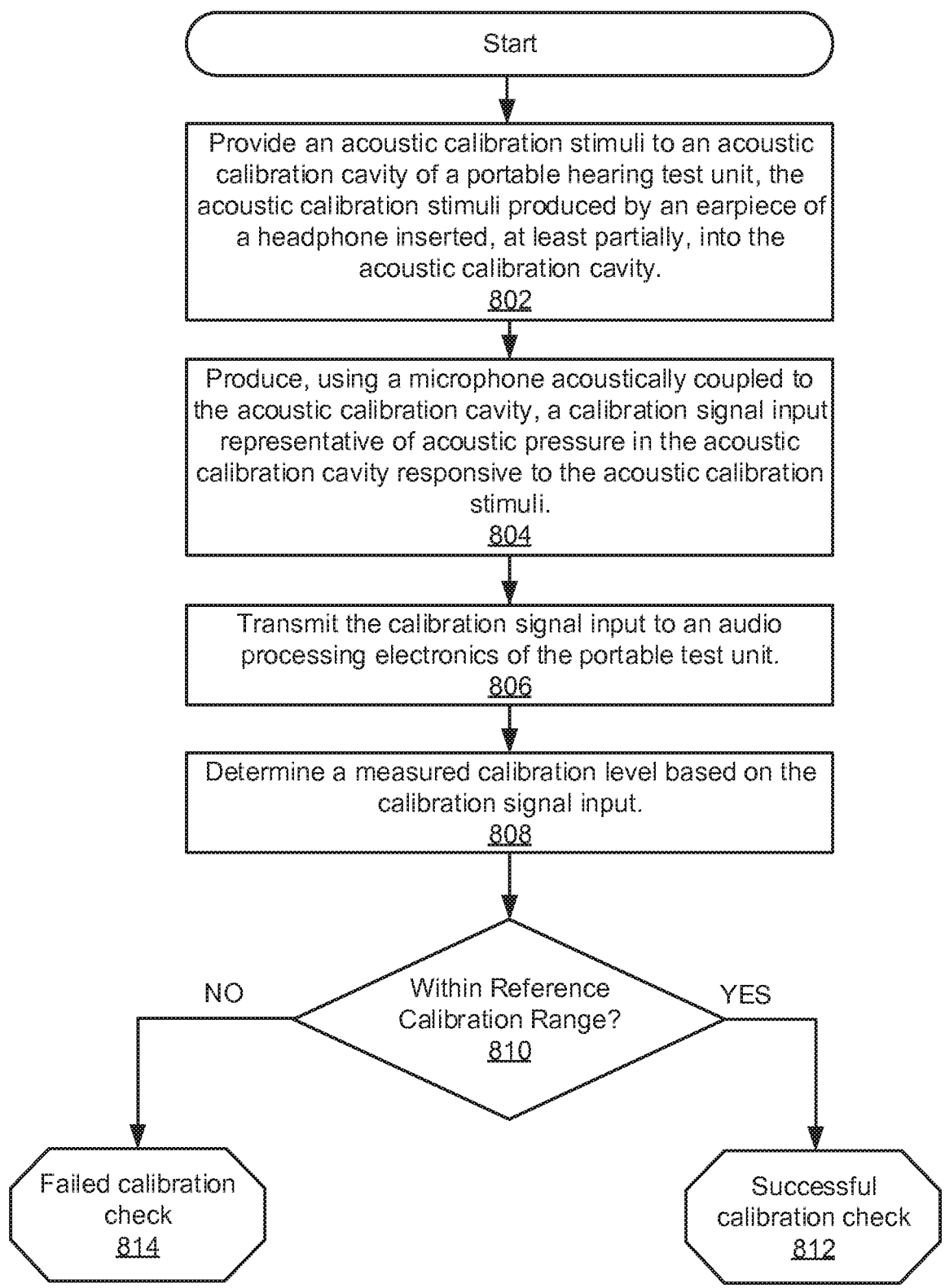
FIG. 8 is a flow chart representation for a calibration check of a hearing test system, according to some examples.

A hearing test system (e.g., hearing test system 100) may be calibrated according to the examples herein. During a calibration check or during a self-calibration, earpiece 30 may receive a calibration signal to cause earpiece 30 to generate an acoustic calibration stimuli for conducting a calibration check or self-calibration. The earpiece 30 may produce an acoustic calibration stimuli by audio streaming from the computing device 40. For example, during a calibration check or during a self-calibration, the headphone 36 may be communicatively coupled to a computing device 40 and may receive the calibration signal from the computing device 40. The earpiece 30 may produce an acoustic calibration stimuli in response to the calibration signal received from the computing device 40. In some examples, the headphone 36 may be communicatively coupled to the portable test unit 10. e.g., via an audio interface, such as an audio jack 25 or Bluetooth as described herein. The portable test unit 10 may send the calibration signal to the headphone 36, and the earpiece 30 may produce an acoustic calibration stimuli in response to the calibration signal received from the portable test unit 10. The calibration signal may be generated by the portable test unit 10 based on calibration data (e.g., production calibration data 29) stored in memory. The earpiece 30 may be coupled to any of the computing device 40 and the portable test unit 10 for receiving the calibration signal via a wired or wireless connection. The acoustic calibration stimuli may be generated using the speaker 34 within the earpiece 30. The production calibration data 29 may be adjusted according to reference calibration data 46 stored in memory, as shown in FIGS. 7-8, such that the acoustic calibration stimuli produced by the earpiece is ensured to be within a reference calibration level range. The memory may be associated with the hearing test system 100, for example memory 17 of the portable test unit 10, memory 44 of the computing device 40, or memory of a remote database on.

In some examples, the portable test unit 10 may be communicatively coupled to the computing device 40. The computing device 40 may be a personal computer, a smartphone, or a tablet. The portable test unit 10 may be communicatively coupled to the computing device 40 using a wired connection or a wireless connection. In some examples, the computing device 40 may be coupled to the portable test unit 10 using a wired interface, such as USB in some examples, the computing device 40 may be coupled to the portable test unit 10 using a wireless connection, such as Bluetooth. A processor (CPU) 41 of the computing device 40 may execute a software application 47 stored in memory 44 of the computing device 40. The software application 47 may be browser-based or a standalone application. The software application 47 may include instructions 45 for performing a calibration check or a self-calibration using the portable test unit 10 comprising an acoustic calibration cavity 12 as described herein. A calibration check may verify that the hearing test system 100 is within a reference calibration range with a pass/fail result. A self-calibration may check that the hearing test system 100 is within the reference calibration range, and adjust calibration data (e.g., production calibration data 29) of the hearing test system 100 to recalibrate if the hearing test system 100 is determined to be outside the reference calibration range.

The software application 47 may include functionality for sending commands to the portable test unit 10, such as a command to an audio processing electronics 14 to produce a calibration signal to cause the earpiece 30 to generate acoustic calibration stimuli. The acoustic calibration stimuli may be received by the portable test unit 10 (e.g., by microphone 16) when the earpiece 30 and portable test unit 10 are operatively coupled via the acoustic calibration cavity 12. In some examples, the software application 47 may include functionality for causing a calibration signal to be transmitted to the headphone 36 (e.g., via the portable test unit 10 or directly from the computing device 40 which may be operatively coupled to headphone 36) such that an acoustic calibration stimulus may be produced by the earpiece 30 in response to the calibration signal. The software application 47 may include functionality for retrieving test data from the portable test unit 10, such as calibration levels determined based on measurements from the acoustic calibration cavity 12. The computing device 40 may store, utilize, or relay reference calibration data for performing a calibration check according to examples herein. In some examples, the same software application 47 or a second software application may include functionality for performing a hearing test.

Figure 2:
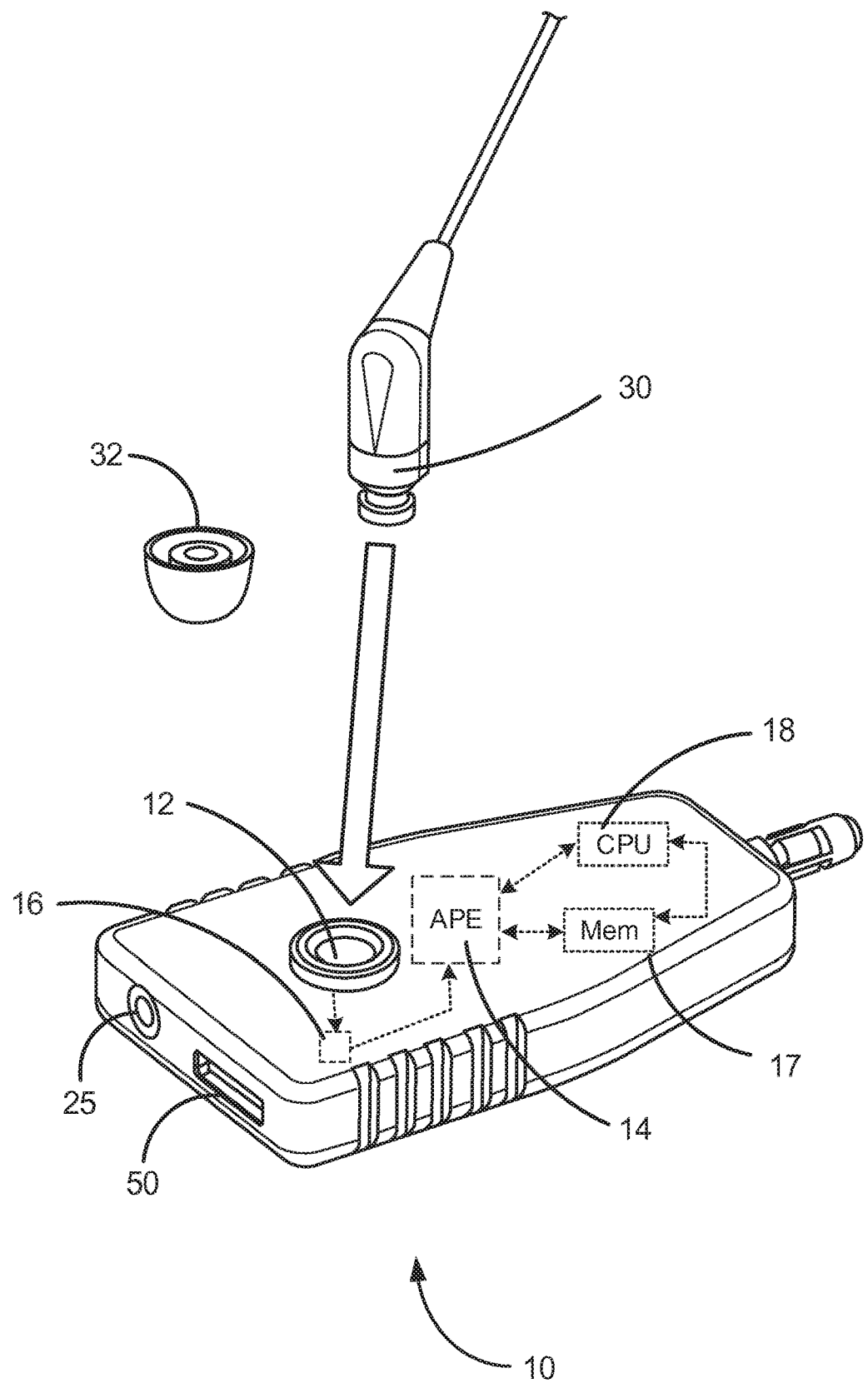
FIG. 2 is a view of a portable test unit including an acoustic calibration cavity provided along an exterior surface adapted to accommodate at least a portion of an earpiece, according to some examples.
Figure 3:
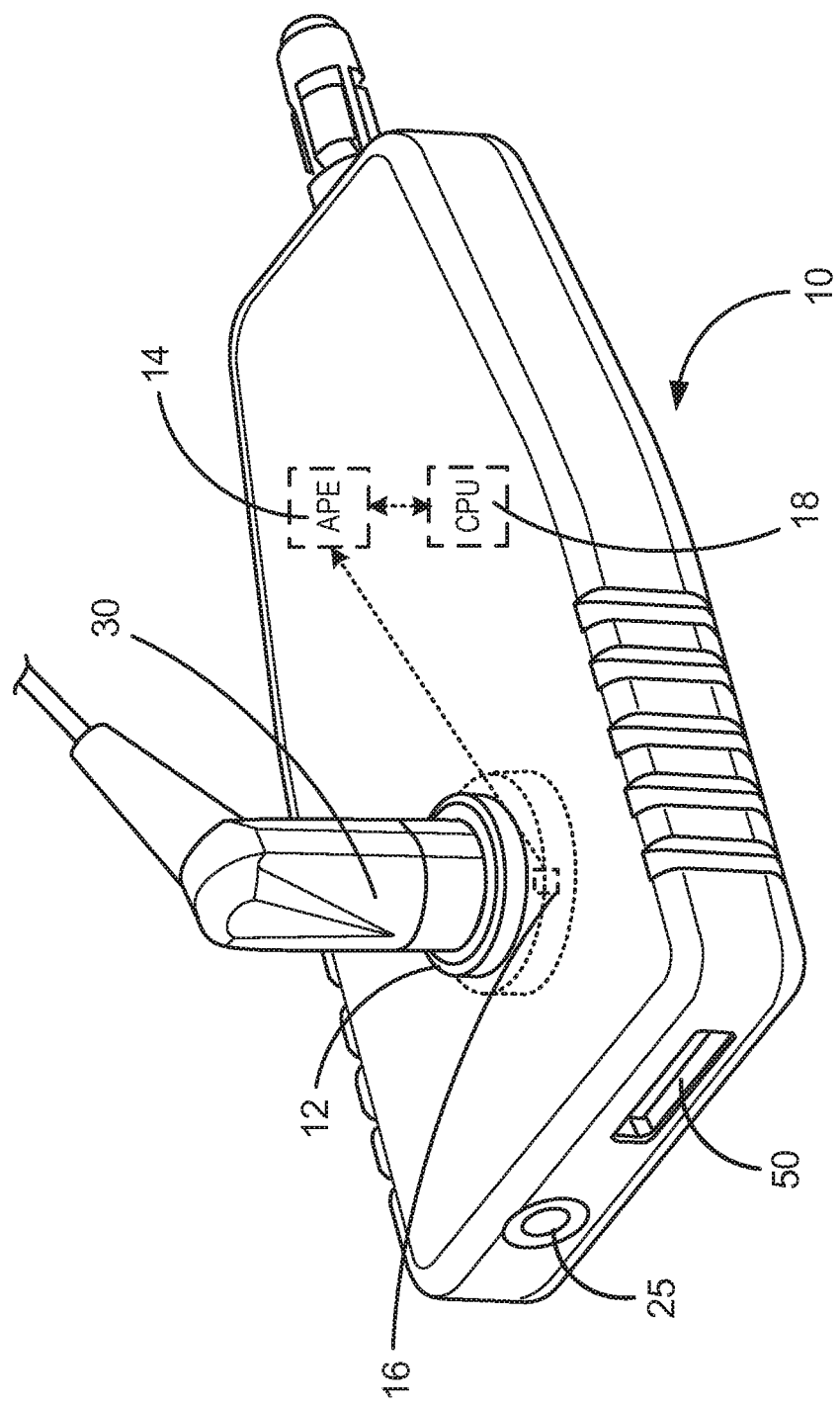
FIG. 3 is a view of a portable test unit with an earpiece inserted in the acoustic calibration cavity, according to some examples.

As described herein and with further reference to FIG. 2, the hearing test system 100 includes a portable test unit 10, which includes an acoustic calibration cavity 12 (also referred to herein as "calibration cavity") adapted to accommodate the earpieces 30 at least partially within. The acoustic calibration cavity 12 may be configured for coupling the earpiece 30 therewith, for example by inserting at least a portion of the earpiece 30 within an opening of the calibration cavity 12 (e.g., an inlet of the calibration cavity 12). In some examples, during a calibration check or a self-calibration, the speaker 34 of the earpiece 30 may be oriented toward a microphone 16 provided within the acoustic calibration cavity 12. In some examples, the microphone 16 may be positioned at a bottom side of the acoustic calibration cavity 12. During a calibration check or a self-calibration, the microphone 16 may produce a calibration signal input in response to the acoustic calibration stimuli generated by the earpiece 30 and provided into the calibration cavity 12. The microphone 16 may deliver the calibration signal input to an audio processing electronics 14 (APE) of the portable test unit 10.

The microphone 16 may measure ambient sounds during a hearing test. For example, during a hearing test, ambient sound may be measured by the microphone 16 to ensure that the ambient sound level is sufficiently low to accurately evaluate the hearing ability of the user 1. Thus, the same hardware of the portable test unit 10 (e.g., microphone 16 and APE 14) may be utilized for the hearing test, calibration check, and/or automatic self-calibration.

As shown in FIGS. 1-2, earpiece 30 of hearing test system 100 may include an ear tip 32 for use during a hearing test. In some examples, the ear tip 32 is removed from the earpiece 30 prior to inserting the earpiece 30 into the acoustic calibration cavity 12 for calibration check. The calibration cavity 12 may be sized and shaped to produce a predetermined sound pressure within the calibration cavity 12 in response to the acoustic calibration stimuli. The acoustic calibration cavity 12 may be configured to provide a controlled acoustic transfer function for the earpiece 30 when inserted at least partially therein. In some examples, the calibration cavity 12 may be configured such that the speaker 34 of the earpiece 30 and the microphone 16 of the portable test unit 10 are oriented towards one another when the earpiece 30 is placed at least partially within the calibration cavity 12. The calibration cavity 12 may alternatively be configured such that the microphone 16 is positioned indirectly with respect to the speaker 34 when the earpiece 30 is placed at least partially within the calibration cavity 12. In some examples, the calibration cavity 12 may secure the earpiece 30 at least partially within the calibration cavity 12 using locking tabs, notches, detents, pressure fit, treads, any other type of known securing features, or combinations thereof.

Figure 4:
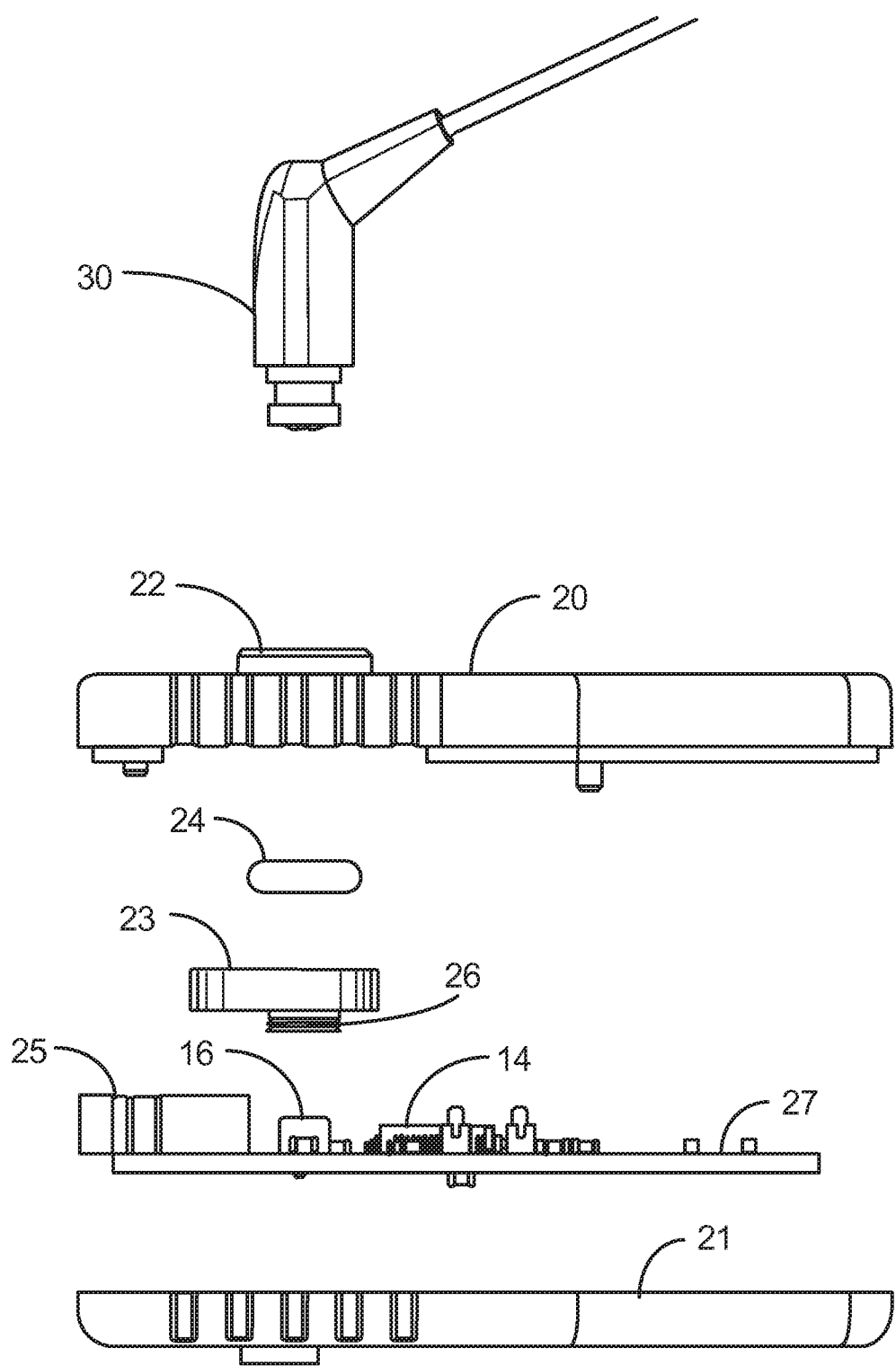
FIG. 4 is an exploded view of a portable test unit and an earpiece showing an acoustic calibration cavity, according to some examples.
Figure 5:
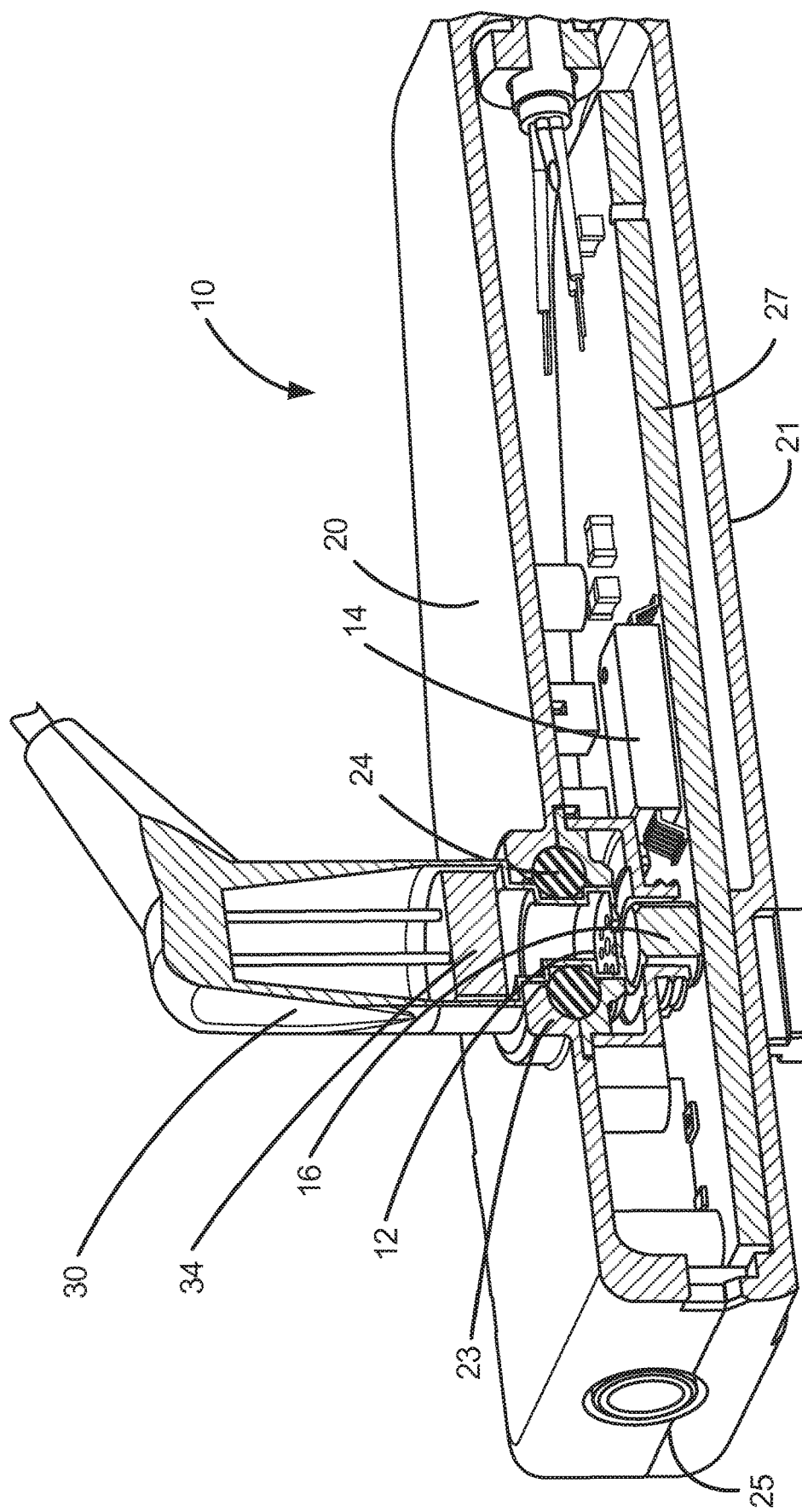
FIG. 5 is a sectional view of a portable test unit with an earpiece partially inserted into the acoustic calibration cavity, according to some examples.
Figure 6:
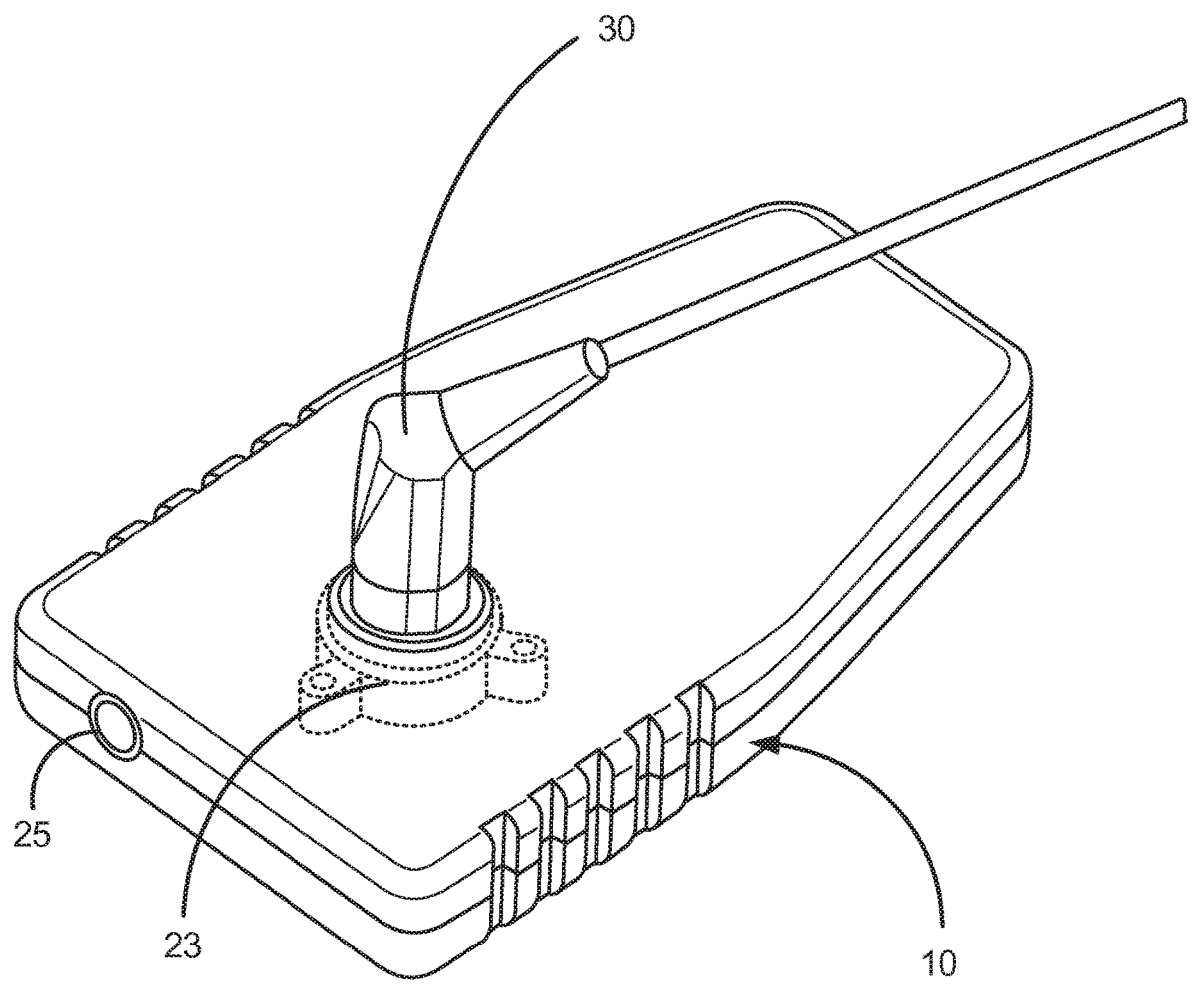
FIG. 6 is a top view of a portable test unit with an earpiece coupled thereto, according to some examples.

FIGS. 4-6 provide additional views of portable test unit 10 and earpiece 30 according to the present disclosure. FIG. 4 is an exploded view of a portable test unit 10 and an earpiece 30, according to some examples. The portable test unit 10 may include a housing that encapsulates electronic circuitry (e.g., audio processing electronics 14) therein. The housing may be formed from plastic. The housing may be manufactured using an injection molding process or any other known methods. The housing may include a top housing component 20 and a bottom housing component 21 that may couple with one another by adhesive, snapping, ultrasonic welding, or any other known bonding mechanism or technique. The top housing component 20 may include a cavity opening 22 which may function as an inlet to the acoustic calibration cavity 12 of the portable test unit 10. The cavity opening 22 may be configured for cooperating fit with the earpiece 30 when inserted at least partially therein. The cavity opening 22 may be circular, semi-circular, or any other shape to match the shape of the earpiece 30 to be inserted at least partially therein. The acoustic calibration cavity 12 may include a lead in feature and a sealing ring 24 to facilitate insertion and acoustic sealing of the earpiece 30 when the earpiece 30 is coupled to the acoustic calibration cavity 12. The acoustic calibration cavity 12 may define an acoustic chamber providing predefined acoustics, thus providing a controlled calibration check. The acoustic calibration cavity 12 may be provided between the top housing component 20 and the bottom housing component 21. In some examples, the acoustic calibration cavity 12 may be formed by a calibration cavity compartment 23 placed inside the upper and lower housings as shown in FIG. 4. The calibration cavity compartment 23 may be shaped and sized to provide a controlled acoustic transfer function between the earpiece 30 and microphone 16 of the portable test unit 10. The acoustic calibration cavity compartment 23 may further include a bottom cavity opening 26. The bottom cavity opening 26 may accommodate the microphone 16, which may be provided on a circuit board 27 of the portable test unit 10, at least partially therein. The bottom cavity opening 26 may acoustically couple the earpiece 30 to the microphone 16 when the earpiece 30 is at least partially inserted into the acoustic calibration cavity 12. The portable test unit 10 may include an acoustic seal for acoustical sealing of the earpiece 30 when coupled thereto. An acoustic seal in the form of sealing ring 24 may be provided within the calibration cavity 12 to seal the earpiece 30 when placed at least partially therein. Sealing for either the earpiece 30 and/or the microphone 16 may be an O-ring type, made of compliant material such as rubber. Sealing of the microphone 16 to the calibration cavity compartment 23 may also be achieved by the use of a sealing adhesive.

In some examples, the acoustic calibration cavity 12 may be formed by a molded part to produce a precise and controlled acoustic transfer function when the earpiece 30 is at least partially inserted therein. The calibration cavity 12 may be cylindrically shaped to match the shape of a cylindrical earpiece 30. The calibration cavity volume may be in the range of about 0.1 to about 0.5 cc, which may reduce or minimize the size of the portable test unit 10. Other shapes and configurations of the calibration cavity 12 may be used depending on the shape and type of the headphone 36 used in a hearing test system 100, e.g., for administering a hearing evaluation. In some examples, the calibration cavity 12 may be sized and shaped to accommodate and test the calibration of a hearing device 60, when placed at least partially therein.

FIG. 5 is a sectional view and FIG. 6 is a top isometric view of a portable test unit 10 with an earpiece 30 coupled thereto, according to some examples. The portable test unit 10 may include a circuit board 27 within the housing of the portable test unit 10. Certain circuitry of the portable test unit 10 may be provided on the circuit board 27. The circuit board 27 may be rigid or flexible for incorporating and connecting the electronics and transducers, such as the microphone 16 and user activated switches. The portable test unit 10 may include interface ports (also referred to as I/O interfaces), for example an audio jack 25 for coupling the headphone 36 and for connecting to a communications port. The audio jack 25 may be used to couple the portable test unit 10 and the headphone 36 during a hearing test, a calibration check, or a self-calibration. During a hearing test, an earpiece 30 of the headphone 36 may be worn by the user 1 in the ear. During a calibration check or a self-calibration, an earpiece 30 of the headphone 36 may be inserted into the calibration cavity 12. In some examples, the I/O interfaces may include wired ports such as a USB port or wireless connection interfaces such as a Bluetooth interface. In some examples, the portable test unit 10 may be connected to a computing device 40 by a USB connection. In some examples, the circuitry may provide wireless connectivity, for example a Bluetooth integrated circuit and an antenna. In some examples, the I/O interfaces of portable test unit 10 may include a programming interface 50 as described herein.

A calibration test or self-calibration check may be performed to validate a calibration of the hearing test system 100 and correspondingly of stimuli produced by the hearing test system 100. The calibration of the hearing test system 100 may be validated by coupling any of the earpieces 30 of the headphone 36 to the acoustic calibration cavity 12 as described above. When the earpiece 30 is properly inserted into the acoustic calibration cavity 12, the audio processing electronics 14 may execute instructions 19 to transmit a calibration signal to the earpiece 30. The calibration signal may be generated by the audio processing electronics 14 and transmitted to the earpiece 30 using a wired connection (e.g., via audio jack 25) or a wireless connection (e.g., Bluetooth). The acoustic calibration signal may be generated using calibration data, for example production calibration data 29. The production calibration data 29 may be stored in memory (e.g., memory 17 of the portable test unit 10, memory 44 of the computing device 40, or on a remote database). Acoustic pressure produced in response to the calibration stimuli provided in the calibration cavity 12 may be sensed by the microphone 16. The microphone 16 may generate a calibration signal input in response to the sensed acoustic pressure. The calibration signal input may be representative of the acoustic calibration stimuli provided into calibration cavity 12. The calibration signal input from the microphone 16 may be transmitted to the audio processing electronics 14, and the audio processing electronics 14 may determine a measured calibration level based on the sensed acoustic pressure. The measured calibration level may be compared with a reference calibration level to validate the calibration of the hearing test system 100. In some examples, the production calibration data 29 may be automatically adjusted according to the measured calibration level. For example, and as noted herein, production calibration data 29, which may be used to produce signals for generating acoustic calibration stimuli (e.g., acoustic test stimuli and/or calibration stimuli), may be stored in a memory of the hearing test system 100 or memory communicatively coupled with the hearing test system 100. If the measured calibration level is not within an acceptable range, the production calibration data 29 associated with heating test system 100 may be adjusted such that acoustic stimuli generated by the hearing test system in a subsequent hearing test or calibration correspond with stimuli that are associated with the reference levels. The production calibration data 29 for the earpiece 30 may be automatically adjusted, e.g., without further human involvement, responsive to the measured calibration level if different from the acceptable range relative to the reference level. In some examples, the audio processing electronics 14 and processor 18 are incorporated into a single chip integrated circuit (IC), incorporating a CPU, an analog-to-digital (A/D) converter, and a digital-to-analog (D/A) converter.

The reference calibration data 46 may be stored in memory 17 within the portable test unit 10, or in the memory of an external device, for example the memory 44 of the computing device 40 or memory of a remote database accessible by the heating test system 100. The reference calibration data 46 may be generated at the factory. The production calibration data 29 may include data representative of acoustic calibration stimuli matching the reference calibration data 46. The audio processing electronics 14 may be in communication with one or more I/O devices, for example a wireless antenna or a USB bus. The audio processing electronics 14 may receive a calibration signal input produced by the microphone 16. The calibration signal input produced by the microphone 16 may be in response to receiving acoustic calibration stimuli produced by the speaker 34 of the earpiece 30 when seated properly within the calibration cavity 12. In some examples, the calibration signal may be a tonal signal, composite signal, or wide spectrum noise, representing the range of audiometric frequencies of interest for the hearing test system 100 and the calibration of transducers thereof.

The audio processing electronics 14 may be incorporate an internal processor 18. The internal processor 18 or an external processor 41 (collectively, the "processors") within the computing device 40 may be configured to measure a calibration level of the hearing test system 100 and perform additional functions for validating the calibration of and/or re-calibrating the hearing test system 100. The calibration level may be determined from a voltage level of the calibration signal input which may be representative of the level of the acoustic calibration stimuli produced by speaker 34. The processors may validate the measured calibration level using reference calibration data 46 stored in memory. The reference calibration data 46 may be retrieved from local memory (e.g., memory 44 of the computing device 40 or memory 17 of the portable test unit 10) or from memory of a remote server. The validation may occur by comparing the measured calibration level to a reference level. The measured calibration level may be validated if the calibration level is within an acceptable range, for example within 1-3 dB of a reference calibration level. The acceptable range may be any tolerance level determined to be acceptable, and may be within 3 dB for frequencies in the range of 500 to 4,000 Hz. according to certain standards, such as the ANSI 3.6 Standard for Audiometers. In some examples, the tolerance level may be greater than 3 dB.

If the calibration level for a particular frequency is validated, the processors may proceed to check the calibration at other frequencies until all audiometric frequencies of interest are validated. If the measured calibration level is found to be outside an acceptable range, the processors may adjust the production calibration data 29 to compensate for the out-of-range calibration. In some examples, a failed calibration check may require the portable test unit 10 or the headphone 36 to be sent to the manufacturer or a service center for inspection or re-calibration. A failed calibration check may be indicative of a damaged headphone 36, a leaky acoustic calibration cavity 12, or a defective connection or electronic component. A leaky acoustic calibration cavity 12 may result from a cracked cavity compartment 23 or a damaged sealing ring 24.

A processor associated with the hearing test system 100 may use the measured calibration level to ensure that the portable test unit 10 is within the acceptable range with respect to the reference calibration level.

In some examples, the acoustic calibration stimuli delivered into the calibration cavity 12 may be above 60 dB SPL to minimize interference from ambient sounds present in the environment of the portable test unit 10 during the calibration check or during the automatic calibration process.

The self-checking hearing test system 100 disclosed herein may reduce or eliminate costly calibration checks, or recalibration, typically performed at the manufacturer site, or by a technician in clinical settings. The hearing test system 100 may allow for self-checking of the integrity of the portable test unit 10 and/or headphone 36 at home or non-clinical setting by a non-expert user by inserting the earpiece 30 of the headphone 36 into the calibration cavity 12 and initiating a calibration check by a software application 47. In some examples, the calibration check is rapid and takes less than 15 seconds. In some examples, acoustic calibration stimuli at multiple test frequencies, for example 500, 1,000, 2000 and 4,000 Hz, may be produced and provided into the calibration cavity 12 and the measured calibration level at each test frequency may be compared with reference levels (e.g., as obtained from stored reference calibration data). In some examples, the calibration stimuli may represent a composite signal including a plurality of audiometric frequencies, for example the audiometric frequencies of interest. In some examples, calibration data, for example production calibration data 29 associated with hearing test system 100, may be adjusted to yield measured calibration levels within a reference calibration range for the calibration cavity 12. This self-contained calibration system may mitigate the need for specialized calibration instruments such as a sound level meter, an acoustic coupler, and/or a sound level meter calibrator unit.

In some examples, the hearing test system 100 may include a hearing aid fitting capability. A hearing test system 100 according to such examples may utilize the audio processing electronics 14 for delivering calibrated audio signals at predetermined levels to a non-acoustic input of a programmable hearing device (e.g., hearing device 60 in FIG. 9) in-situ. The test audio signals may correspond to sound segments of varied sound levels and frequency characteristics. The hearing test system 100 may also include a programming port or interface 50 for interactively delivering audio and/or programming signals to a programmable hearing device in-situ. The programming interface 50 may be wired or wireless. In some examples, a wired programming interface 50 may include a programming pod to couple the portable test unit 10 to a programmable hearing device. The programming pod may be provided on a first end of a programming cable. A second end of the programming cable may couple to the programming interface 50. In some examples, the portable test unit 10 may include a power source, for example a battery. In some examples, the portable test unit 10 may draw power from the computing device 40 using a wired interface, such as USB. The programming pod may deliver power and allow for data communications between the portable test unit 10 and the programmable hearing device. In some examples, at least a portion of the programming pod provided on the first end of the programming cable may be inserted into a receptacle cavity of a main module of the programmable hearing device. In some examples, an I/O plug (e.g., USB) provided on the second end of the programming cable may be mechanically and electrically coupled to the portable test unit 10 at the programming interface 50.

A fitting method according to examples herein may generally involve instructing a user 1 (e.g., a hearing device consumer) to listen to the output of the hearing device 60 in-situ and to adjust fitting parameters 63 (e.g., via a user interface 43) according to the subjective assessment of the consumer to the output delivered by the hearing device 60 in-situ, said output generated by interactively delivering a test audio signal and programming signals to the hearing device 60 in-situ. The fitting method may be implemented by software application 47 or another software application stored in memory 44 of the computing device 40. A user interface 43, e.g. for use during a fitting method, may be presented to the user using a display 42 of the computing device 40. The user interface 43 may be configured to allow the hearing device consumer to respond and adjust hearing device parameters 63 in perceptual lay terms, such as volume, loudness, audibility, clarity, and the like, rather than technical terms and complex graphical tools conventionally used by hearing professionals in clinical settings. The fitting of the hearing device 60 enables the user 1 to customize the hearing device 60 such that the speaker 61 of the hearing device 60 produces an output in response to signals received by the hearing device 60 based on the preferences and/or hearing impairment of the user 1.

FIGS. 7-8 are flow charts of methods one or both of which may be embodied in a hearing test system according to some examples of the present disclosure. While the various steps in these flow charts are presented and described sequentially, one of ordinary skill will appreciate that some or all of the steps can be executed in different orders and some or all of the steps can be executed in parallel. Further, in some examples, one or more of the steps described below can be omitted, repeated, and/or performed in a different order. Accordingly, the specific arrangement of steps shown in FIGS. 7-8 should not be construed as limiting the scope of the invention.

FIG. 7 is a flow chart of a method of calibration check of a hearing test system comprising a built-in calibration cavity (e.g., acoustic calibration cavity 12), according to some examples. In step 702, an acoustic calibration stimuli is provided to an acoustic calibration cavity of a portable test unit. The acoustic calibration stimuli may be produced by an earpiece of a headphone inserted, at least partially, into the acoustic calibration cavity. In step 704, a calibration signal input is produced using a microphone acoustically coupled to the acoustic calibration cavity. The calibration signal input may be representative of acoustic pressure in the acoustic calibration cavity responsive to the acoustic calibration stimuli. In step 706, the calibration signal input is transmitted to audio processing electronics of the portable test unit. In step 708, a measured calibration level based on the calibration signal input is determined. In step 710, if the measured calibration level is outside a predefined calibration range, an action to calibrate is performed. A determination may be made as to whether the measured calibration level is within an acceptable range of calibration. If yes, then the self-calibration may terminate as shown in step 712. If no, then the calibration data may be adjusted using the measured calibration level as shown in step 714. Any of steps 702, 704, 706, 708, and 710 may then be repeated for each frequency to be calibrated. Alternatively, a composite signal representing a multitude of audiometric frequencies may be produced and a corresponding calibration signal input may be produced and analyzed using the appropriated processing, for example by Fast Fourier Transform (FFT) analysis. It will be understood that any of the steps described above may be repeated or cycled through until a determination is made that the level of the calibration signal input is within the acceptable range of calibration.

FIG. 8 is a flow chart of a method for performing a calibration check of a hearing test system, according to some examples. In step 802, an acoustic calibration stimuli is provided to an acoustic calibration cavity of a portable test unit. The acoustic calibration stimuli may be produced by an earpiece of a headphone inserted, at least partially, into the acoustic calibration cavity. In step 804, a calibration signal input is produced using a microphone acoustically coupled to the acoustic calibration cavity. The calibration signal input may be representative of acoustic pressure in the acoustic calibration cavity responsive to the acoustic calibration stimuli. In step 806, the calibration signal input is transmitted to audio processing electronics of the portable test unit. In step 808, a measured calibration level based on the calibration signal input is determined. In step 810, a determination may be made as to whether the level of the calibration signal input is within a calibration range. The calibration range may be in accordance with reference calibration data stored in a memory. A remote server and/or a computing device may host any of the calibration range, production calibration data, and the reference calibration data. If yes, then a successful calibration check is indicated as shown in step 812. If no, then a failed calibration check is indicated as shown in step 814.

Although embodiments of the invention are described herein, variations and modifications of these embodiments may be made, without departing from the true spirit and scope of the invention. Thus, the above-described embodiments of the invention should not be viewed as exhaustive or as limiting the invention to the precise configurations or techniques disclosed. Rather, it is intended that the invention shall be limited only by the appended claims and the rules and principles of applicable law.

What is claimed is:

1. A hearing test system comprising:
a headphone comprising an earpiece;
a portable test unit comprising:
an acoustic calibration cavity comprising a first opening along an exterior surface of the portable test unit for receiving the earpiece, and a second opening, wherein the acoustic calibration cavity is shaped to provide a controlled acoustic transfer function for the earpiece;
a microphone acoustically coupled to the acoustic calibration cavity at the second opening, the microphone configured to receive acoustic calibration stimuli from the earpiece and produce a calibration signal input in response to the acoustic calibration stimuli; and audio processing electronics in electronic communication with the microphone for receiving the calibration signal input from the microphone; and a processor communicatively coupled to the audio processing electronics and configured to determine a calibration level based on the calibration signal input.

2. The hearing test system of claim 1, wherein the processor is further configured to validate a calibration of the hearing test system by comparing the calibration level with a calibration reference level.

3. The hearing test system of claim 1, wherein the processor is further configured to receive calibration data from any of a remote server, a client computer, and a memory of the portable test unit.

4. The hearing test system of claim 1, wherein the processor is configured to adjust calibration data based on the calibration level, and wherein the acoustic calibration stimuli is produced using the calibration data.

5. The hearing test system of claim 1, wherein the portable unit comprises a sealing ring proximate to the first opening of the acoustic calibration cavity, the second opening of the acoustic calibration cavity, or both.

6. The hearing test system of claim 1, wherein the earpiece is configured for partial insertion into an ear canal during administration of a hearing test.

7. The hearing test system of claim 1, further comprising a plurality of ear tips of different sizes, each configured to couple with the earpiece.

8. The hearing test system of claim 1, further comprising a programming interface configured for programming a programmable hearing device.

9. A hearing evaluation system comprising:

an earpiece comprising a speaker configured to produce acoustic calibration stimuli;

a portable test unit comprising:
an acoustic calibration cavity comprising an opening along an exterior surface of the portable test unit, wherein the opening is configured to accommodate the earpiece at least partially within such that the speaker is acoustically coupled to the acoustic calibration cavity, and wherein the acoustic calibration cavity is shaped to provide a controlled acoustic transfer function for the earpiece;

a microphone acoustically coupled to the acoustic calibration cavity, wherein the portable test unit is configured to produce a calibration signal and deliver the calibration signal to the earpiece for producing the acoustic calibration stimuli when the earpiece is placed at least partially within the acoustic calibration cavity; and a computing device configured to couple with the portable test unit, the computing device configured to perform a calibration measurement of the acoustic calibration stimuli when the earpiece is placed at least partially within the acoustic calibration cavity.

10. The hearing test system of claim 9, wherein the portable test unit and the computing device are coupled using a USB connection.

11. The hearing test system of claim 9, wherein the portable test unit and the computing device are communicatively coupled using a wireless interface.

12. The hearing test system of claim 9, wherein the wireless interface is Bluetooth.

13. The hearing test system of claim 9, wherein the microphone is configured to receive the acoustic calibration stimuli produced by the earpiece.

14. A portable test unit comprising:

an acoustic calibration cavity comprising an opening along an exterior surface of the portable test unit, wherein the acoustic calibration cavity is configured to accommodate an earpiece at least partially within for acoustically coupling a speaker of the earpiece to the acoustic calibration cavity, and wherein the acoustic calibration cavity is shaped to provide a controlled acoustic transfer function for the earpiece;

a microphone acoustically coupled to the acoustic calibration cavity, the microphone configured to receive an acoustic calibration stimuli from the earpiece when the earpiece is coupled thereto and produce a calibration signal input responsive to the acoustic calibration stimuli; and audio processing electronics which transmit an acoustic calibration signal to the earpiece when the earpiece is coupled thereto and receive the calibration signal input from the microphone.

15. The portable test unit of claim 14, further comprising a processor configured to validate a calibration of the portable test unit by determining a measured calibration level responsive to the calibration signal input and comparing the measured calibration level with a reference calibration level.

16. The portable test unit of claim 14, wherein the audio processing electronics communicatively couples to processor external to the portable test unit, wherein the processor is configured to validate a calibration of the portable test unit by determining a measured calibration level responsive to the calibration signal input and comparing the measured calibration level with a reference calibration level.

17. A method of performing a calibration check of a personal hearing test system comprising:

providing a portable test unit of the personal hearing test system, wherein the portable test unit comprises an acoustic calibration cavity having an opening along an exterior surface of the portable test unit and a microphone acoustically coupled to the acoustic calibration cavity, wherein the opening is configured to receive an earpiece for acoustically coupling a speaker of the earpiece to the acoustic calibration cavity, and wherein the acoustic calibration cavity is shaped to provide a controlled acoustic transfer function for the earpiece;

providing an acoustic calibration stimuli to the acoustic calibration cavity by the earpiece when inserted, at least partially, into the opening;

producing, using the microphone, a calibration signal input representative of acoustic pressure in the acoustic calibration cavity resulting from the acoustic calibration stimuli;

transmitting the calibration signal input to an audio processing electronics of the portable test unit;

determining a measured calibration level based on the calibration signal input; and indicating if the calibration level is within or outside a calibration range.

18. The method of claim 17 further comprising accessing a computing device to retrieve a calibration data.

19. The method of claim 17, further comprising adjusting a calibration data stored in memory based on the measured calibration level.

20. The method of claim 19, further comprising comparing the calibration level to the calibration range to determine whether the measured calibration level is within the calibration range.

21. The method of claim 17, wherein the acoustic calibration stimuli is produced by the earpiece using a calibration data.

* * * * *